United States Patent
Yamada

(10) Patent No.: US 9,520,277 B2
(45) Date of Patent: Dec. 13, 2016

(54) SUBSTANCE IDENTIFICATION METHOD AND MASS SPECTROMETRY SYSTEM USED FOR THE SAME METHOD

(71) Applicant: SHIMADZU CORPORATION, Kyoto-shi, Kyoto (JP)

(72) Inventor: Yoshihiro Yamada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 856 days.

(21) Appl. No.: 13/848,324

(22) Filed: Mar. 21, 2013

(65) Prior Publication Data
US 2013/0253848 A1 Sep. 26, 2013

(30) Foreign Application Priority Data
Mar. 22, 2012 (JP) ................................ 2012-064806

(51) Int. Cl.
H01J 49/00 (2006.01)
G06F 19/00 (2011.01)

(52) U.S. Cl.
CPC ........... *H01J 49/0036* (2013.01); *G06F 19/70* (2013.01); *G06F 19/703* (2013.01); *H01J 49/004* (2013.01)

(58) Field of Classification Search
CPC .................... G01N 33/6848; H01J 49/0036
USPC ...................... 250/281; 702/27, 23
See application file for complete search history.

(56) References Cited

U.S. PATENT DOCUMENTS

| | | | | |
|---|---|---|---|---|
| 8,530,831 B1* | 9/2013 | Coon | ................ | G01N 33/6848 250/281 |
| 9,043,164 B2* | 5/2015 | Makarov | ............. | H01J 49/0036 702/27 |
| 2005/0063864 A1* | 3/2005 | Sano | ................ | G01N 33/6848 422/68.1 |

FOREIGN PATENT DOCUMENTS

| | | |
|---|---|---|
| JP | 2004-257922 A | 9/2004 |
| JP | 3766391 B2 | 4/2006 |

OTHER PUBLICATIONS

Japanese Office Action issued Mar. 24, 2015 in corresponding Japanese Patent Application 2012-064806.
(Continued)

*Primary Examiner* — Andrew Schechter
*Assistant Examiner* — Kaleria Knox
(74) *Attorney, Agent, or Firm* — Sughrue Mion, PLLC

(57) ABSTRACT

An identification probability estimation model, which shows the relationship between the S/N ratios of $MS^1$ peaks and the cumulative number of the peaks in the case where $MS^2$ measurements and identifications is performed in descending order of S/N ratio, is created beforehand from the S/N ratios of $MS^1$ peaks as well as the results of $MS^1$ or $MS^2$ measurements and identifications (success or failure) performed for a number of fractionated samples obtained from a predetermined sample. Based on an evaluated value of the identification probability and that of the identification probability increment, an order of priority of $MS^2$ measurements for a plurality of $MS^1$ peaks is determined, and an $MS^2$ measurement sequence which gives the maximal expectation value of the number of substances to be identified under a limitation on the number of $MS^2$ measurements or other factors is determined.

12 Claims, 8 Drawing Sheets

(56) References Cited

OTHER PUBLICATIONS

Aleskey Nakorchevsky et al., "Exploring Data-Dependent Acquisition Strategies with the Instrument Control Libraries for the Thermo Scientific Instruments", The Schipps Research Institute, 58th ASMS Conference, 2010, 1 pg.

* cited by examiner

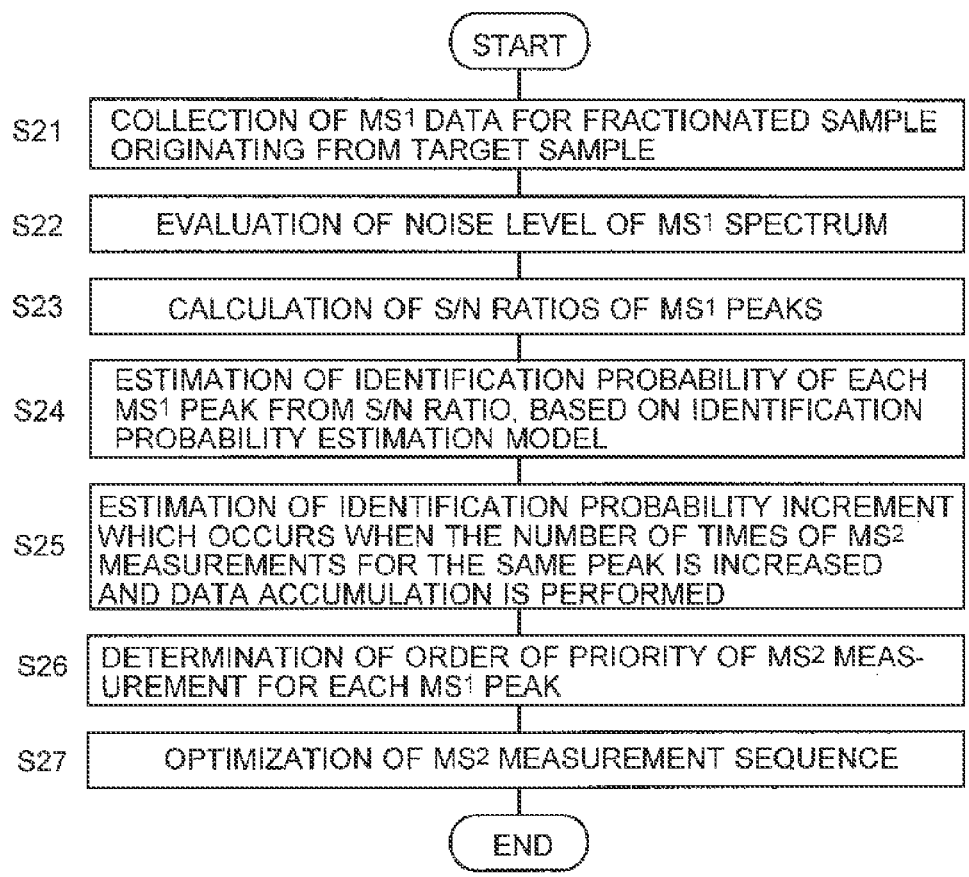

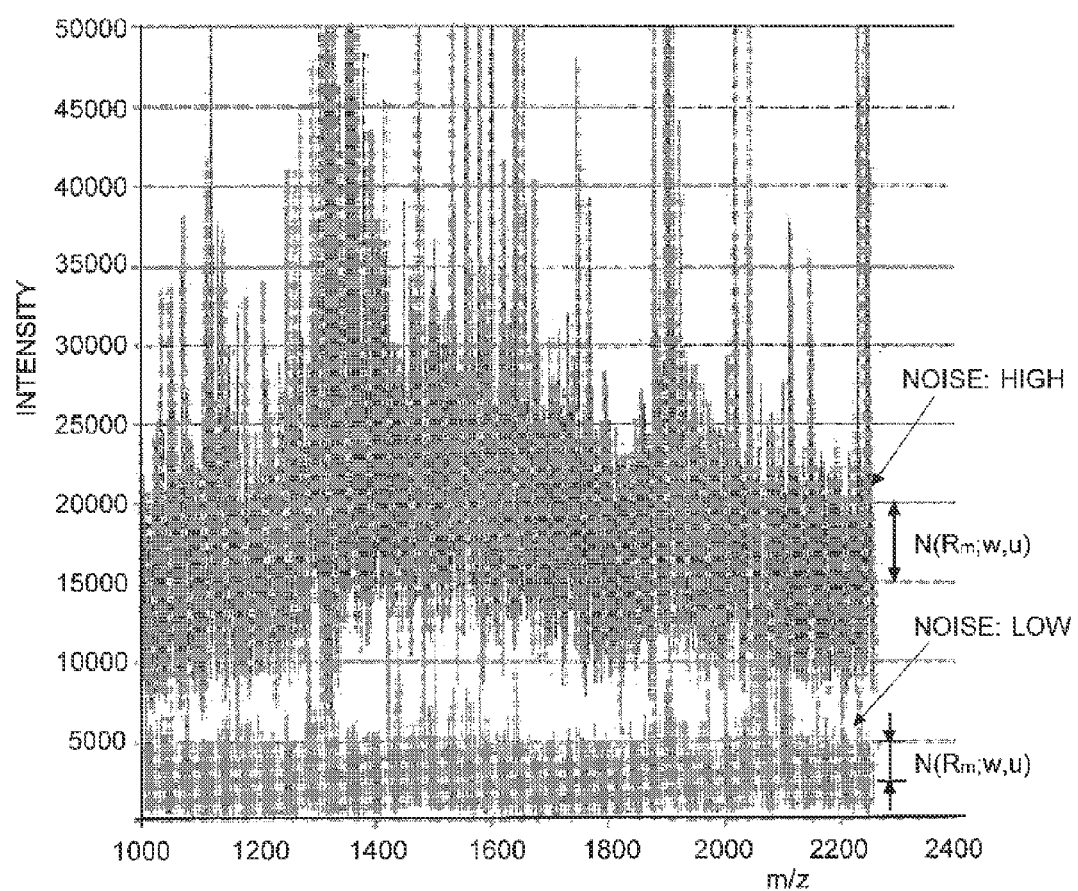

SUBSTANCE IDENTIFICATION METHOD AND MASS SPECTROMETRY SYSTEM USED FOR THE SAME METHOD

TECHNICAL FIELD

The present invention relates to a method for identifying a substance or substances contained in a sample by using a mass spectrometer capable of an $MS^n$ measurement (where n is an integer equal to or greater than two), and a mass spectrometry system for identifying a substance or substances contained in a sample by using the same method.

BACKGROUND ART

In bioscience research, medical treatment, drug development and similar fields, it has become increasingly important to examine biological samples to comprehensively identify various substances, such as proteins, peptides, nucleic acids and sugar chains. In particular, when aimed at proteins or peptides, such a comprehensive analysis method is called "shotgun proteomics." For such analyses, the combination of a chromatographic technique, such as a liquid chromatograph (LC) or capillary electrophoresis (CE), with an $MS^n$ mass spectrometer (tandem mass spectrometer) has proven itself to be a very powerful technique.

A procedure of a commonly known method for comprehensively identifying various kinds of substances in a biological sample by means of an $MS^n$ mass spectrometer is as follows:

[Step 1] Various substances contained in a sample to be analyzed are separated by an appropriate method, e.g. LC or CE. The thereby obtained eluate is preparative-fractionated to prepare a number of small amount samples. (Each of the small amount samples obtained by preparative fractionation is hereinafter called the "fractionated sample.") The preparative fractionation of a sample should be performed in such a manner that small amount samples are collected either continuously at regular predetermined intervals of time or constantly in the same amount so that every substance in the sample will be included in one of the fractionated samples without fail.

[Step 2] For each fractionated sample, an $MS^1$ measurement is performed to obtain an $MS^1$ spectrum, and a peak or peaks that are likely to have originated from a substance or substances to be identified are selected on the $MS^1$ spectrum.

[Step 3] Using the peak selected in Step 2 as the precursor ion, an $MS^2$ measurement for the fractionated sample concerned is performed. Then, based on the result of this measurement, a database search or de novo sequencing is performed to identify a substance or substances contained in the fractionated sample.

[Step 4] If no specific substance has been identified with sufficient accuracy, an $MS^2$ measurement using another peak on the $MS^1$ spectrum as the precursor ion is performed, or a higher-order $MS^n$ measurement (i.e. n=3 or greater) using a specific ion observed on the $MS^2$ spectrum as the precursor ion is performed. Then, a database search, de novo sequencing or similar data processing based on the result of the measurement is performed to identify a substance or substances contained in the fractionated sample.

[Step 5] The processes of Steps 2 through 4 are performed for each of the fractionated samples to comprehensively identify various substances contained in the original sample.

To identify each of the substances with high accuracy by the previously described comprehensive identification process, it is desirable that each fractionated sample should contain a small number of kinds of substances (most desirably, only one kind). To achieve this, it is necessary to shorten the period of each fractionating cycle, which significantly increases the number of cycles of fractionation. Considering that, to identify as many substances as possible within a limited length of measurement time or with a limited number of times of measurements, i.e. to improve the throughput of the comprehensive identification of one or more substances contained in a fractionated sample, it is necessary to preferentially select, as the precursor ion, one or more peaks having a higher probability of successful identification (which is hereinafter called the "identification probability") among the peaks observed on the $MS^1$ spectrum and perform the $MS^n$ analysis under appropriate measurement conditions.

One conventional method for selecting a precursor ion for an $MS^2$ measurement from the peaks observed on an $MS^1$ spectrum obtained for a given sample is to sequentially select the peaks on the spectrum in descending order of intensity (see Patent Document 1). For example, if the length of time for the $MS^2$ measurement of one sample is limited, the system is controlled so that a predetermined number of peaks will be sequentially selected as the precursor ion in descending order of their intensities. In another commonly known method, all the peaks, without limiting the number of peaks, whose intensities are equal to or greater than a predetermined threshold are selected as precursor ions, provided that the measurement can be performed for an adequate length of time or an adequate number of times.

These methods seem to entirely rely on the assumption that using an ion having a higher peak intensity ensures a higher identification probability. Although this assumption is not qualitatively wrong, it should be noted that the peak intensity does not always correspond to the value of identification probability. For example, suppose that there are multiple peaks that can be chosen as a precursor ion. In some cases, choosing any one of these peaks will result in successful identification with high probability, while in other cases successful identification can be expected only when a specific peak among them is chosen. Quantitatively discriminating between such different situations from the peak intensity beforehand is considerably difficult. Thus, there has been no established method for quantitatively evaluate the identification probability of each peak on an $MS^1$ spectrum beforehand, i.e. before the execution of an $MS^2$ measurement, and this is one of the major factors which decrease the efficiency of the comprehensive identification.

BACKGROUND ART DOCUMENT

Patent Document

Patent Document 1: JP-B 3766391

Non-Patent Document

Non-Patent Document 1: Aleksey Nakorchevsky et al., "Exploring Data-Dependent Acquisition Strategies with the Instrument Control Libraries for the Thermo Scientific Instruments", 58th ASMS Conference, 2010

SUMMARY OF THE INVENTION

Problem to be Solved by the Invention

Conversely, if the identification probability of each peak on the $MS^{n-1}$ spectrum can be quantitatively evaluated, it will be possible to select a more appropriate peak as the precursor ion or sequentially select a plurality of peaks as the precursor ion in a more appropriate order, based on the result of the quantitative evaluation. To address such a problem, the applicant of the present patent application has proposed, in Japanese Patent Application No. 2011-244600 (which corresponds to U.S. patent application Ser. No. 13/670,396), a new technique of quantitatively estimating the probability of substance identification using a result of an $MS^2$ measurement before actually performing the $MS^2$ measurement.

Thus, the primary objective of the present invention is to provide a substance identification method in which the technical idea of the identification probability estimation method proposed in the aforementioned patent application is used to identify a large number of substances efficiently, i.e. with high reliability based on mass spectrometric data obtained by the smallest possible number of measurements or in the shortest possible measurement time, as well as a mass spectrometry system for such a method.

Means for Solving the Problems

A first aspect of the present invention aimed at solving the previously described problem is a substance identification method for identifying a substance contained in each of a plurality of fractionated samples obtained by separating various substances contained in a sample according to a predetermined separation parameter and fractionating the sample, based on $MS^{n-1}$ spectra obtained by $MS^{n-1}$ measurements (where n is an integer equal to or greater than two) respectively performed for the plurality of fractionated samples, including:

a) an identification probability estimation model creation step, in which an identification probability estimation model is created by using signal-to-noise ratios of $MS^{n-1}$ peaks found by $MS^{n-1}$ measurements for a plurality of fractionated samples obtained from a predetermined sample and the results of substance identification based on the results of $MS^{n-1}$ measurements using each of the $MS^{n-1}$ peaks as a precursor ion, the model showing a relationship between the signal-to-noise ratios of a plurality of $MS^{n-1}$ peaks originating from the same kind of sample and the cumulative number of peaks successfully identified through a series of $MS^n$ measurements and identifications in which the $MS^{n-1}$ peaks are sequentially selected as a precursor ion in order of the signal-to-noise ratios thereof, and identification probability estimation model information representing the identification probability estimation model is stored;

b) a peak signal-to-noise ratio calculation step, in which, after an $MS^{n-1}$ measurement for at least one fractionated sample obtained from a target sample to be identified has been completed, a signal-to-noise ratio is calculated for each of a plurality of $MS^{n-1}$ peaks selected as the candidates of the precursor ion from among the $MS^{n-1}$ peaks found by the $MS^{n-1}$ measurement;

c) an identification probability estimation step, in which an estimated value of the identification probability of each of the $MS^{n-1}$ peaks is calculated from the signal-to-noise ratios of the $MS^{n-1}$ peaks calculated in the peak signal-to-noise ratio calculation step, with reference to the identification probability estimation model derived from the identification probability estimation model information; and d) an $MS^n$ measurement order determination step, in which an order of priority of the $MS^n$ measurements for the plurality of $MS^{n-1}$ peaks selected as the candidates of the precursor ion is determined, using the estimated value of the identification probability calculated for each of the $MS^{n-1}$ peaks.

A second aspect of the present invention aimed at solving the previously described problem is a mass spectrometry system used for identifying a substance or substances contained in each of a plurality of fractionated samples obtained by separating various substances contained in a sample according to a predetermined separation parameter and fractionating the sample, based on $MS^n$ spectra obtained by $MS^n$ measurements (where n is an integer equal to or greater than two) respectively performed for the plurality of fractionated samples, including:

a) an identification probability estimation model information memory for storing identification probability estimation model information representing an identification probability estimation model which shows a relationship between signal-to-noise ratios of a plurality of $MS^{n-1}$ peaks originating from the same kind of sample and the cumulative number of $MS^n$ peaks successfully identified through a series of $MS^n$ measurements and identifications in which the $MS^{n-1}$ peaks are sequentially selected as a precursor ion in order of the signal-to-noise ratios thereof, the identification probability estimation model being created by using the signal-to-noise ratios of $MS^{n-1}$ peaks found by $MS^{n-1}$ measurements for a plurality of fractionated samples obtained from a predetermined sample and the results of substance identification based on the results of $MS^{n-1}$ measurements using each of the $MS^{n-1}$ peaks as a precursor ion;

b) a peak signal-to-noise ratio calculator, which, after an $MS^{n-1}$ measurement for at least one fractionated sample obtained from a target sample to be identified has been completed, calculates a signal-to-noise ratio for each of a plurality of $MS^{n-1}$ peaks selected as the candidates of the precursor ion from among the $MS^{n-1}$ peaks found by the $MS^{n-1}$ measurement;

c) an identification probability estimator for calculating an estimated value of the identification probability of each of the $MS^{n-1}$ peaks from the signal-to-noise ratios of the $MS^{n-1}$ peaks calculated by the peak signal-to-noise ratio calculator, with reference to the identification probability estimation model derived from the identification probability estimation model information; and d) an $MS^n$ measurement order determiner for determining an order of priority of the $MS^n$ measurements of the plurality of $MS^{n-1}$ peaks as the candidates of the precursor ion, using the estimated value of the identification probability calculated for each of the $MS^{n-1}$ peaks, and the system performing the $MS^n$ measurements for the aforementioned fractionated samples according to the order of priority determined by the $MS^n$ measurement order determiner.

In the present invention, the separation of various kinds of substances contained in a sample can be achieved by a liquid chromatograph (LC), capillary electrophoresis or any other means. In the case of the LC or similar device using a column, the aforementioned separation parameter is time (retention time). This means that one fractionated sample contains one or more substances eluted from the column within a predetermined range of time. In the case of using CE to separate various kinds of substances contained in a sample, the separation parameter is mobility.

There is no limitation on the method for identifying a substance or substances based on an $MS^n$ spectrum. For example, de novo sequencing, MS/MS ion search or any algorithm can be used. It should be noted that the same algorithm must be used both in the identification process performed in the identification probability estimation model creation step (or by the identification probability estimation model creation step) and in the identification process performed on a sample of interest obtained from a target sample.

In the identification probability estimation model creation step of the substance identification method according to the first aspect of the present invention, the identification probability estimation model information is determined by using data in which the $MS^{n-1}$ measurements, the $MS^n$ measurements and the results of identification performed by using the outcome of the $MS^n$ measurements (i.e. whether or not the identification was successful) are completely present. The identification probability estimation model shows a relationship between the signal-to-noise ratios of a plurality of $MS^{n-1}$ peaks (normally, a considerable number of peaks) and the cumulative number of peaks which will be successfully identified through a series of $MS^n$ measurements and identifications with each of the $MS^{n-1}$ peaks sequentially selected as a precursor ion in ascending or descending order of their signal-to-noise ratios. Accordingly, this identification probability estimation model indicates the proportion of $MS^{n-1}$ peaks having signal-to-noise ratios higher or lower than that of an $MS^{n-1}$ peak exhibiting a certain signal-to-noise ratio in all the $MS^{n-1}$ peaks. A signal-to-noise ratio of an $MS^1$ peak can be computed from the signal intensity of this $MS^1$ peak and the noise level calculated from the $MS^1$ spectrum (with a profile before undergoing a noise removal or other processing) which contains the same peak.

Specifically, the relationship between the cumulative number of $MS^{n-1}$ peaks sequentially selected in ascending or descending order of signal-to-noise ratio and the total number of successfully identified $MS^{n-1}$ peaks will be shaped like a line which increases in a staircase pattern. Accordingly, in the identification probability estimation model creation step, for example, a fitting for determining a continuous relationship between the cumulative number of $MS^n$ peaks and the number of successful identifications may be performed to obtain a smooth fitting curve, and a function formula or one or more coefficients and/or constants included in the function formula may be used as the identification probability estimation model information.

An appropriate identification probability estimation model depends on the kind of sample, or more exactly, on the kinds of substances contained in the sample. In other words, the same identification probability estimation model information can be used in the case of identifying the same kind or a similar kind of substance. For example, when the measurement is aimed at identifying proteins in a biological sample, the identification probability estimation model information can be previously prepared on the basis of $MS^{n-1}$ peaks or other data obtained for a preparatory sample containing various kinds of previously identified proteins.

For a plurality of $MS^{n-1}$ peaks observed on an $MS^{n-1}$ spectrum obtained by an $MS^{n-1}$ measurement for one fractionated sample obtained from a sample containing unknown substances, the signal-to-noise ratio of each $MS^{n-1}$ peak is calculated in the peak signal-to-noise calculation step, for example, before the $MS^n$ measurement is performed. The method of calculating the signal-to-noise ratio must be the same as used in the creation of the identification probability estimation model. In the identification probability estimation step, an estimated value of the identification probability of each $MS^{n-1}$ peak is calculated from its signal-to-noise ratio, with reference to the identification probability estimation model derived from the identification probability estimation model information. Thus, the probability of successful identification of an $MS^{n-1}$ peak based on the result of an $MS^n$ measurement of the peak can be quantitatively estimated without actually performing the $MS^n$ measurement. In the $MS^n$ measurement order determination step, an order of priority of the $MS^n$ measurements for a plurality of $MS^{n-1}$ peaks selected as the candidates of the precursor ion is determined, using the estimated value of the identification probability calculated for each of the $MS^{n-1}$ peaks in the aforementioned manner.

For example, in the case where the number of $MS^{n-1}$ peaks to be extracted as a candidate of the precursor ion for one fractionated sample exceeds the number of $MS^n$ measurements allowed to be performed for one fractionated sample, the $MS^{n-1}$ measurements can be performed for a predetermined number of candidates of the precursor ion in the previously described order of priority. In this case, no $MS^n$ measurement will be performed for one or more low-priority candidates of the precursor ion.

Conversely, in the case where the number of $MS^n$ measurements allowed to be performed for one fractionated sample exceeds the number of $MS^{n-1}$ peaks to be extracted as the candidates of the precursor ion for one fractionated sample, it is possible to perform the $MS^n$ measurement for one $MS^{n-1}$ peak a plurality of times and accumulate $MS^n$ spectrum data obtained by the $MS^n$ measurements. Accumulating $MS^n$ spectrum data makes the signal-to-noise ratio of the $MS^n$ spectrum higher than the level before the accumulation, so that an improvement in the identification probability is expected. A higher original identification probability does not always lead to a higher degree of improvement in the identification probability. Therefore, when the $MS^n$ measurements for the $MS^{n-1}$ peaks are performed for the second or third time (or even more), it is preferable to determine the order of priority based on not the estimated value of the identification probability but the degree of improvement in the identification probability.

Accordingly, in one preferable mode of the substance identification method according to the first aspect of the present invention:

the method further includes an identification probability increment estimation step, in which an estimated increment of the identification probability, which shows a degree of increase in the identification probability achieved by performing an $MS^n$ measurement for the same $MS^{n-1}$ peak a plurality of times and accumulating the results of the measurement, is calculated from the estimated value of the identification probability calculated for each of a plurality of $MS^{n-1}$ peaks selected as the candidates of the precursor ion in the identification probability estimation step; and in the $MS^{n-1}$ measurement order determination step, the order of priority of the $MS^n$ measurements for a plurality of $MS^{n-1}$ peaks under the condition that a plurality of $MS^n$ measurements are allowed for the same $MS^{n-1}$ peak is determined based on the estimated value of the identification probability of each $MS^{n-1}$ peak calculated in the identification probability estimation step and the increment of the identification probability estimated in the identification probability increment estimation step.

The mass spectrometry system according to the second aspect of the present invention can also be constructed in a similar manner.

The previously described substance identification method may preferably include an $MS^n$ measurement sequence determination step, in which a measurement sequence for performing $MS^n$ measurements for a plurality of $MS^{n-1}$ peaks is determined, based on the order of priority determined in the $MS^n$ measurement order determination step and the signal-to-noise ratio of each $MS^{n-1}$ peak, under an upper limit of the number of times of the $MS^n$ measurements to be performed for one fractionated sample.

The "measurement sequence" means a procedure of all the $MS^n$ measurements for the same fractionated sample, including the execution of a plurality of $MS^n$ measurements for the same $MS^{n-1}$ peak.

According to this mode of the invention, the measurement sequence is determined so that the expected number of substances to be successfully identified will always be maximized, regardless of how many times the $MS^n$ measurement is performed for one fractionated sample. By this method, the largest possible number of substances can be identified under the same length of measurement time or the same number of times of the measurement.

In a preferable mode of the substance identification method according to the present invention, a measurement for a predetermined sample is performed before the measurement for the target sample, and based on a result of the former measurement, the identification probability estimation model is created in the identification probability estimation model creation step. If the measurement for a predetermined sample prepared for the creation of the identification probability estimation model is performed immediately before the measurement for the target sample, the measurement conditions will be substantially equalized; e.g. the noise environment will be almost the same. This improves the application accuracy of the identification probability estimation model created for the predetermined sample, and thereby improves the accuracy of the estimated value of the identification probability, so that the order of priority can be more accurately determined.

In the substance identification method according to the first aspect of the present invention, it is preferable to determine a measurement sequence of the $MS^n$ measurement for a fractionated sample by a sequential process of the peak signal-to-noise ratio calculation step, the identification probability estimation step, the $MS^n$ measurement order determination step and the $MS^n$ measurement sequence determination step before the $MS^n$ measurement for that fractionated sample is actually performed. In this case, the control of the $MS^n$ measurements becomes simple since the $MS^n$ measurement using each of the $MS^{n-1}$ peaks as the precursor ion can be performed by simply following the measurement sequence determined for one fractionated sample.

In one mode of the substance identification method according to the first aspect of the present invention, a measurement sequence of the $MS^n$ measurement for a fractionated sample is determined by a sequential process of the peak signal-to-noise ratio calculation step, the identification probability estimation step, the $MS^n$ measurement order determination step and the $MS^n$ measurement sequence determination step before the $MS^n$ measurement for that fractionated sample is performed, and after the $MS^n$ measurement according to the measurement sequence is initiated, the measurement sequence is modified by using an identification result obtained in the course of the $MS^n$ measurement.

For example, while $MS^n$ measurements are being performed sequentially for different $MS^{n-1}$ peaks or repeatedly for the same $MS^{n-1}$ peak according to a measurement sequence, if the situation where no substance can be identified from the result of the $MS^n$ measurements has continued, the $MS^n$ measurements according to that measurement sequence may be discontinued at that point in time so as to move to the $MS^n$ measurements and identifications for the next fractionated sample. This is effective for reducing the number of useless executions of the $MS^n$ measurements and avoiding a decrease in the identification probability, which may occur when a certain discrepancy exists between the identification probability estimation model and the actual result of identification.

Effect of the Invention

With the substance identification method according to the first aspect of the present invention and the mass spectrometry system according to the second aspect of the present invention, when a plurality of $MS^{n-1}$ peaks have been extracted from the result of an $MS^{n-1}$ measurement as candidates of the precursor ion, it is possible to select a precursor ion that gives the largest expectation value of the number of substances to be identified, or to determine the order of $MS^n$ measurements for different $MS^{n-1}$ peaks or the same $MS^{n-1}$ peak. Therefore, for example, as many substances as before can be successfully identified in a shorter length of measurement time or with a smaller number of times of measurements. This also means that a greater number of substances can be identified if the length of measurement time or the number of times of measurements is the same as before.

BRIEF DESCRIPTION OF THE DRAWINGS

FIG. 3 is a flowchart showing a process of optimizing an $MS^2$ measurement sequence based on an identification probability estimation model in the substance identification method according to the present invention.

FIG. 5 shows an example of the result of a noise-level calculation for two $MS^1$ profiles.

BEST MODE FOR CARRYING OUT THE INVENTION

One embodiment of the substance identification method according to the present invention, and one embodiment of the mass spectrometry system for performing substance identification by the same method, are hereinafter described in detail, with reference to the attached drawings.

The substance identification method according to the present invention is applied in a mass spectrometry system (or compound identification system) in which, for each of a number of fractionated samples separated and fractionated from a target sample by a liquid chromatograph or similar device, an $MS^{n-1}$ measurement is performed to obtain an $MS^{n-1}$ spectrum, one or more $MS^{n-1}$ peaks are selected as precursor ions, an $MS^n$ measurement is performed for each precursor ion to obtain an $MS^n$ spectrum, and various kinds of substances contained in the target sample are identified by using the $MS^n$ spectrum. The method is characterized by the process of quantitatively estimating the probability of successful identification of a substance for an $MS^1$ peak on an $MS^{n-1}$ spectrum, and on the basis of that probability, optimizing or nearly optimizing the $MS^n$ measurement sequence including the order of selection of $MS^n$ peaks.

A method of optimizing an $MS^n$ measurement sequence according to the present invention is described, taking one concrete example.

In the method according to the present example, an identification probability estimation model is created preliminarily, i.e. in advance of the actual measurement and identification of a target sample to be identified, by using the results of measurements and identifications performed for a sample containing a number of substances for creating an identification probability estimation model (such a sample is hereinafter simply called the "sample for model creation"). The identification probability estimation model serves as reference data for estimating the probability that an $MS^2$ measurement and identification using an $MS^1$ peak as a precursor ion will be successful, before actually performing the $MS^2$ measurement and identification. The sample for model creation should preferably be of the same kind as the target sample; for example, if the target sample is a peptide mixture, the sample for model creation should also be a peptide mixture.

Figure 2:
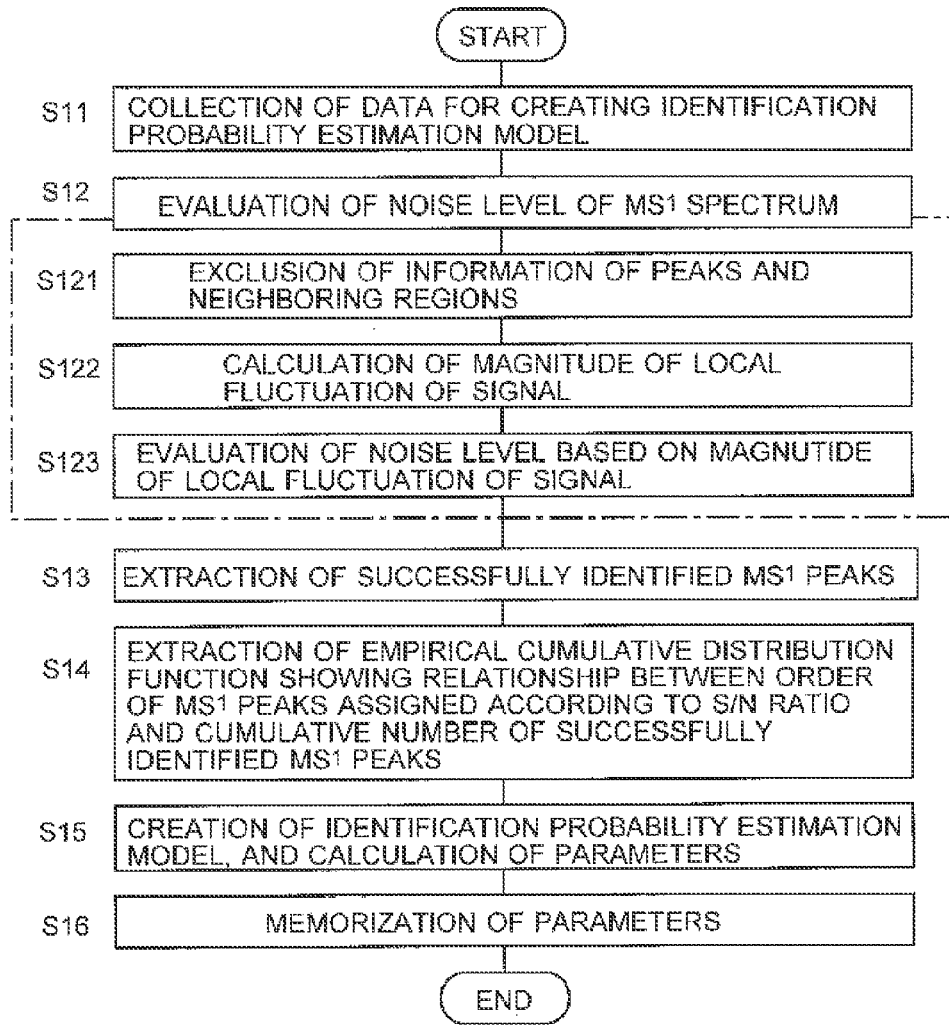
FIG. 2 is a flowchart showing a process of creating an identification probability estimation model in the substance identification method according to the present invention.

FIG. 2 is a flowchart showing the procedure of creating an identification probability estimation model. With reference to this figure, the procedure of creating an identification probability estimation model is hereinafter described in detail.

[Step S11] Collection of Data for Creating Identification Probability Estimation Model A sample for model creation is temporally separated by a liquid chromatograph, and the eluate is repeatedly collected at predetermined intervals of time to prepare a number of fractionated samples. An $MS^1$ measurement is performed for each fractionated sample to collect an $MS^1$ spectrum data. For each $MS^1$ peak extracted from this $MS^1$ spectrum data, an $MS^2$ measurement, which includes one CID (collision induced dissociation) operation, is performed to collect an $MS^2$ spectrum data, and an identification process using this $MS^2$ spectrum data is attempted.

In the case of identifying substances contained in each of the fractionated samples separately collected according to their retention time in the previously described manner, a three-dimensional $MS^1$ spectrum is created by aligning $MS^1$ spectra of the fractionated samples in order of their retention time. For this three-dimensional $MS^1$ spectrum, peak detection is performed on the two-dimensional plane of mass-to-charge ratio m/z and retention time, to extract an $MS^1$ peak. Then, using the mass-to-charge ratio of this $MS^1$ peak as a precursor ion, an $MS^2$ measurement is performed to obtain an $MS^2$ spectrum. Based on this $MS^2$ spectrum, an identification of substances is attempted by a predetermined identification algorithm (such as de novo sequencing or MS/MS ion search). This identification process is performed for each $MS^1$ peak. Whether the attempt of identification has resulted in success or failure (no substances identified) is determined for each $MS^1$ peak extracted from the three-dimensional $MS^1$ spectrum.

[Step S12] Evaluation of Noise Level of $MS^1$ Spectrum

The identification probability, which will be described later, is affected by the noise level of the $MS^1$ spectrum. To deal with this problem, the noise level of the $MS^1$ spectrums obtained from the sample for model creation is evaluated. In the present example, the noise level is evaluated for each fractionated sample, i.e. for each $MS^1$ spectrum, by the following Steps S121-S123, based on an $MS^1$ raw profile (which is hereinafter simply called the "raw profile") created from raw (unprocessed) data obtained by an $MS^1$ measurement. In the following description, the signal intensity of a discretized raw profile is denoted by $R_m$, where m=0, 1, . . . is a number indicating the order of mass-to-charge ratios of the sampling points on the raw profile of a sample to be evaluated. The entire set of the sampling points included in a raw profile is denoted by M.

[Step S121] Exclusion of Information of Peaks and Neighboring Regions

Let $P^{(max)}$ denote the maximum peak intensity of the raw profile. That is to say, $P^{(max)}$ is defined as follows:

$$P^{(max)} = \max_{(m \in M)} R_m \qquad (1).$$

Figure 4A:
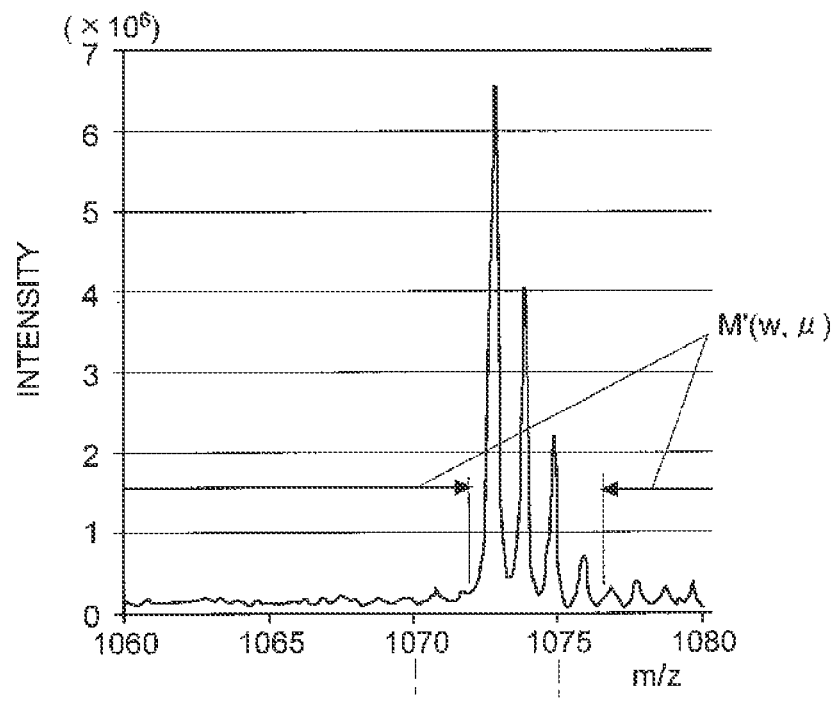
FIGS. 4A and 4B show an example of $MS^1$ profile (mass spectrum) for explaining a noise-level evaluation process.
Figure 4B:
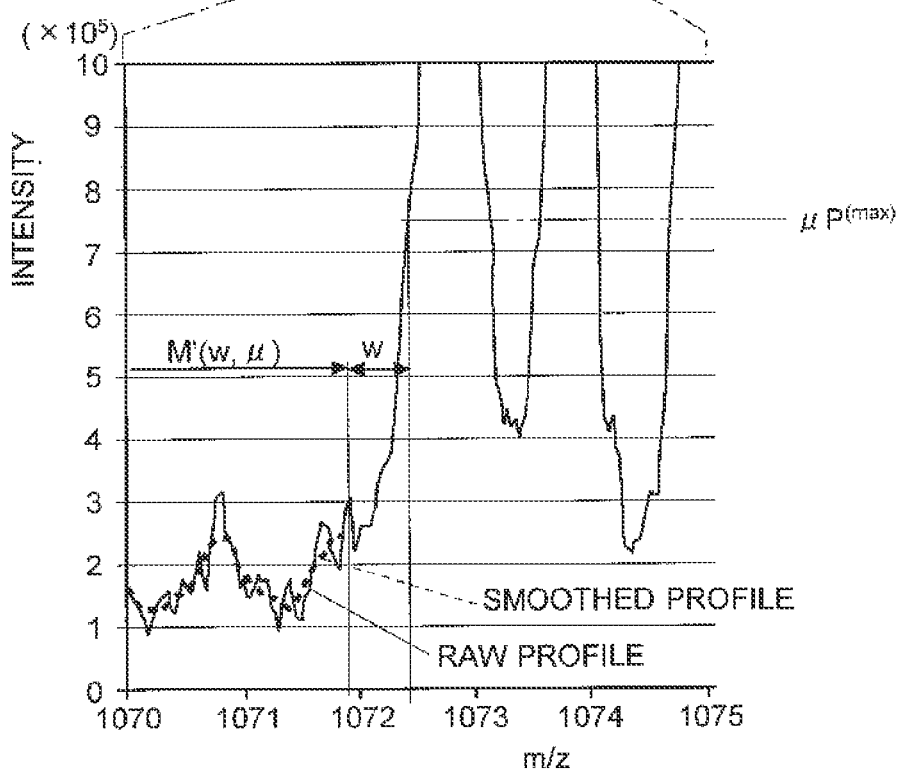

With an appropriately selected threshold $\mu$ for determining the neighboring region of a peak ($0<\mu<1$), any sampling point having a signal intensity equal to or greater than $\mu$ times the $P^{(max)}$ are regarded as the peak portion. A set of sampling points M'(w, $\mu$) which corresponds to the entire group of the sampling points exclusive of those included in the peak portion (i.e. exclusive of any sampling point whose distance from the nearest sampling point having an intensity of $\mu \cdot P^{(max)}$ or greater is equal to or smaller than w) is determined. For example, FIG. 4A shows a set of sampling points M'(w, $\mu$) determined in a raw profile of an $MS^1$ spectrum within a range from m/z 1060 to m/z 1080, and FIG. 4B is an enlargement of a portion of FIG. 4A, showing a range from m/z 1070 to m/z 1075.

[Step S122] Calculation of Magnitude of Local Fluctuation of Signal

In the set of sampling points M'(w, $\mu$) exclusive of the peaks and neighboring regions, the raw profile is smoothed by a filter with a pass band of half width w, to obtain a smoothed profile $*R_m(w, \mu)$. That is to say, $*R_m(w, \mu)$ is given by the following equation:

$$*R_m(w,\mu) = \{1/(2w+1)\} \Sigma R_{m'} \qquad (2).$$

$$(m' \in M'(w,\mu))$$

In equation (2), $\Sigma$ is the sum of $R_{m'}$ from m'=-w to m'=w. The difference between this smoothed profile $*R_m(w, \mu)$ and the original raw profile is defined as the magnitude of the local fluctuation of the signal, which is hereinafter expressed as $\Delta R_m(w, \mu)$. That is to say, $\Delta R_m(w, \mu)$ is given by the following equation:

$$\Delta R_m(w,\mu) = R_m - {}^*R_m(w,\mu) \quad (3).$$

[Step S123] Calculation of Noise Level Based on Magnitude of Local Fluctuation of Signal In this example, the noise level $N(R_m; w, \mu)$ is defined as the root mean square of the magnitude of the local fluctuation of the signal $\Delta R_m(w, \mu)$ multiplied by c, where c is an appropriate constant for defining the noise level. That is to say, $N(R_m; w, \mu)$ is defined by the following equation:

$$N(R_m;w,\mu) = c \times \sqrt{\Sigma \Delta R_m(w,\mu)^2} \quad (4).$$

It should be noted that the definition of the noise level is not limited to this one; any form of definition is allowed as long as it appropriately represents the noise level of $MS^1$ spectra.

FIG. 5 shows the result of one example in which the noise level $N(R_m; w, \mu)$ was calculated in the previously described manner based on two actually obtained $MS^1$ raw profiles.

[Step S13] Extraction of Successfully Identified $MS^1$ Peaks

Figure 6:
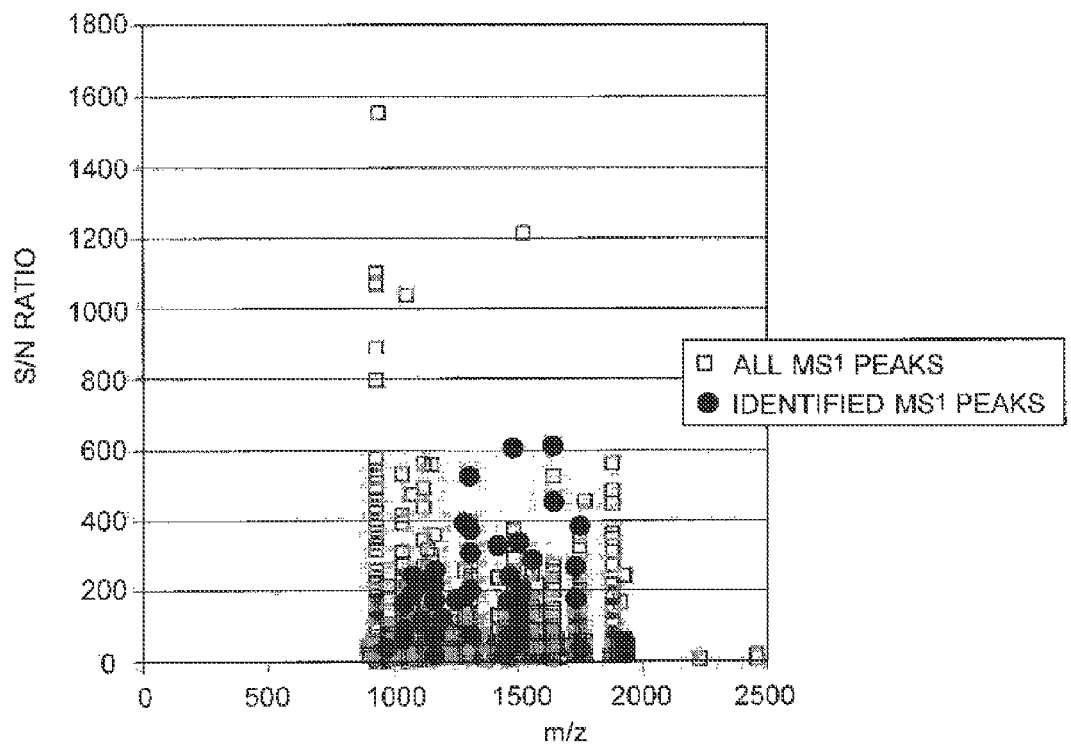
FIG. 6 shows an example of the distribution of $MS^1$ peaks with respect to the mass-to-charge ratio m/z and the signal-to-noise ratio.

FIG. 6 is an example of a chart on which all the $MS^1$ peaks originating from a sample for model creation are plotted with respect to the mass-to-charge ratio m/z and the signal-to-noise (S/N) ratio. The S/N ratio in this chart is the ratio of the peak intensity to the noise level calculated in Step S12. Each of the square plots in FIG. 6 represents one $MS^1$ peak, while each of the circular plots indicates that a substance could be identified by an $MS^2$ measurement using that $MS^1$ peak as the precursor ion, i.e. that the $MS^1$ peak has been successfully identified. FIG. 6 demonstrates that, in the present example, the higher the S/N ratio is, the higher the proportion of successfully identified $MS^1$ peaks will be. This tendency is not specific to the present example but is a general one.

Figure 7:
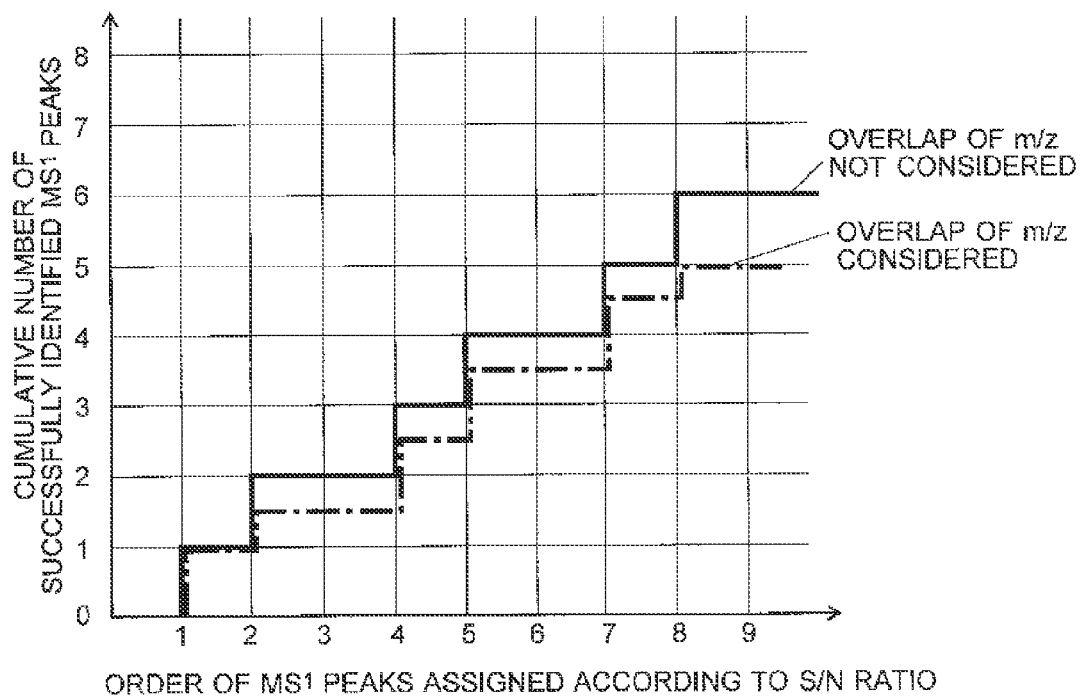
FIG. 7 is a model diagram showing the concept of an empirical cumulative distribution function of successfully identified $MS^1$ peaks in the case where the $MS^1$ peaks are ranked in order of signal-to-noise ratio.

[Step S14] Determination of Relationship Between S/N Ratio of $MS^1$ Peaks and Cumulative Number of Successfully Identified $MS^1$ Peaks If the $MS^1$ peaks are extracted in descending order of S/N ratio and ranked from the $1^{st}$ place (i.e. if the $MS^1$ peaks are sorted and ranked in descending order of S/N ratio), and if the cumulative number of $MS^1$ peaks successfully identified until the process reaches each order is counted, a graph showing the cumulative number increasing rightward a staircase pattern can be drawn, as shown in FIG. 7. The staircase-like polygonal line drawn in the solid line in FIG. 7 shows, for example, that the $MS^1$ peak whose S/N ratio was ranked first was successfully identified, while the identification was unsuccessful for the $MS^1$ peak whose S/N ratio was ranked third and hence lower than that of the first-ranked peak. This polygonal line is an empirical cumulative distribution function which demonstrates how many of the $MS^1$ peaks with S/N ratios equal to or higher than a certain level have been successfully identified.

As can be seen in FIG. 6, in the present example, a plurality of $MS^1$ peaks which correspond to the same mass-to-charge ratio (but whose S/N ratios are not always the same) are individually identified. Accordingly, if the mass-to-ratios are too much overlapped, the result of identification may be relatively too strongly influenced by the overlap of the mass-to-charge ratios. To avoid this problem, in the case where N pieces of $MS^1$ peaks of the same mass-to-charge ratio (where N is an integer equal to or greater than two) have been individually subjected to the identification process, it is preferable to count the individual identification as 1/N in the determination of the empirical cumulative distribution function. In the example shown in FIG. 7, which shows that the identification was successful at the order numbers of 1, 2, 4, 5 and 8, the solid line is an empirical cumulative distribution function for which the overlap of mass-to-charge ratios was not taken into account. In this example, if the successfully identified $MS^1$ peaks ranked at the second and eighth places have the same mass-to-charge ratio, the overlap should be taken into account and each of the $MS^1$ peaks ranked at the second and eighth places should be counted as ½. As a result, the empirical cumulative distribution function will be modified as shown by the chain line in FIG. 7.

Figure 8:
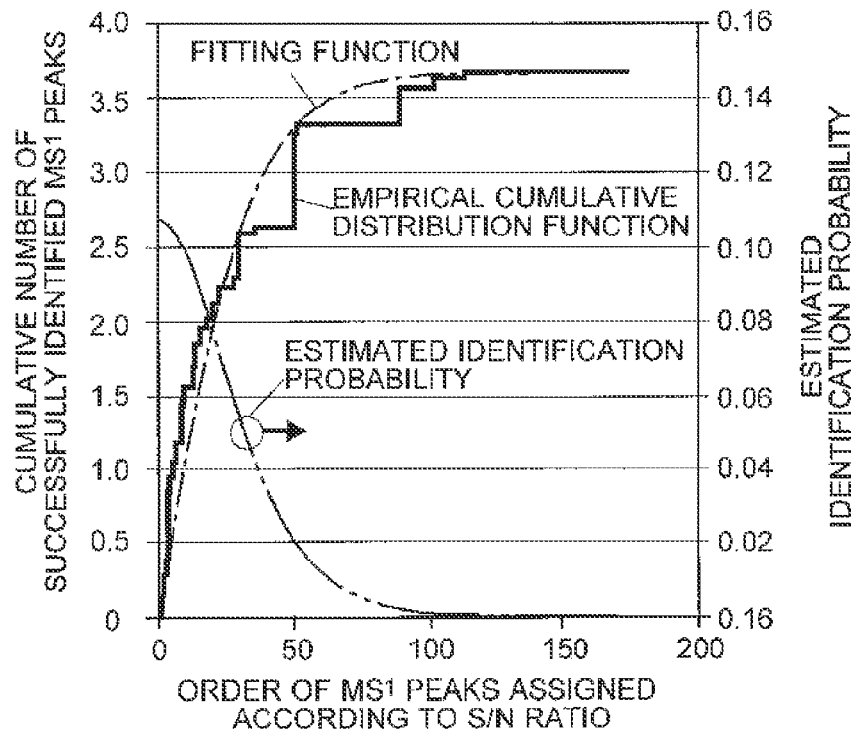
FIG. 8 shows an empirical cumulative distribution function of successfully identified $MS^1$ peaks, a fitting function for that distribution function, and a change in the estimated value of the identification probability based on that fitting function.

For the distribution of successfully or unsuccessfully identified $MS^1$ peaks shown in FIG. 6, if an empirical cumulative distribution function is determined with the overlap of mass-to-charge ratios taken into account in the previously described manner, a staircase-like profile as shown in FIG. 8 is obtained. This profile shows that the larger the order number is (i.e. the lower the S/N ratio of the $MS^1$ peak is), the smaller the number of successfully identified $MS^1$ peaks is, causing the cumulative number of successful identifications to plateau.

[Step S15] Creation of Identification Probability Estimation Model and Calculation of Parameters A fitting operation using an analytical function is performed on the staircase-like profile obtained in Step S14 to determine a smooth curve representing the relationship between the cumulative number of $MS^1$ peaks and that of successful identifications. In the present example, a hyperbolic function expressed by the following equation was used as the fitting function:

$$N^{(ident)} \tan h(n/N^{(all)}\sigma) \quad (5),$$

where n is the number of $MS^1$ peaks ranked higher than a certain level, and $N^{(all)}$ and $N^{(ident)}$ are the total number of $MS^1$ peaks and the number of successfully identified $MS^1$ peaks, respectively. The parameter a determines the rate of rise of the fitting function, the value of which is calculated so that the function will fit the previously determined staircase-like profile. The chain line in FIG. 8 shows the curve that has been fitted to a staircase-like profile. This curve of the fitting function is the identification probability estimation model, and a is the parameter that specifies this model.

When the inclination of the fitting function given by equation (5) is one, it means that the identification will be successful with a probability of 100%, and when the inclination is 0.5, the probability is 50%. Accordingly, by the following equation (6), which is a derivative of the fitting function, the probability of successful identification for a given $MS^1$ peak can be estimated from its order number m:

$$(N^{(ident)}/N^{(all)}\sigma)\sec h^2(n/N^{(all)}\sigma) \quad (6)$$

The estimated identification probability expressed by this derivative is also shown in FIG. 8 in an overlapped form.

Thus, the parameter σ, which determines the identification probability estimation model, can be calculated. Memorizing this parameter σ suffices to estimate the identification probability (Step S16).

Under the condition that the aforementioned parameter of the identification probability estimation model is prepared in advance, an $MS^1$ peak suitable as a precursor ion is selected and an optimal measurement sequence for the $MS^2$ measurement is determined, based on an $MS^1$ spectrum obtained by an $MS^1$ measurement of a fractionated sample prepared by separating and fractionating a target sample by using a liquid chromatograph. The steps of this process are hereinafter described with reference to the flowchart shown in FIG. 3.

[Step S21] Collection of $MS^1$ Measurement Data Originating from Target Sample

Initially, an $MS^1$ measurement is performed for each of a number of fractionated samples prepared from a target sample, to collect $MS^1$ spectrum data. The obtained $MS^1$ spectra of the fractionated samples are aligned in order of retention time to construct a three-dimensional $MS^1$ spectrum. Then, peak detection is performed on the two-dimensional plane of the mass-to-charge-ratio and retention time of this spectrum to extract $MS^1$ peaks. This process is basically the same as Step S11, with a mere difference in what type of sample is used.

[Step S22] Evaluation of Noise Level of $MS^1$ Spectrum

The noise level of the $MS^1$ spectrum of each of the fractionated samples is evaluated by performing the same process as Step S12 (S121-S123).

[Step S23] Calculation of S/N Ratios of $MS^1$ Peaks

For each $MS^1$ peak extracted in Step S21, an S/N ratio is calculated from the intensity of that peak and the noise level calculated in Step S22 for the fractionated sample in which that peak has been found.

Figure 9:
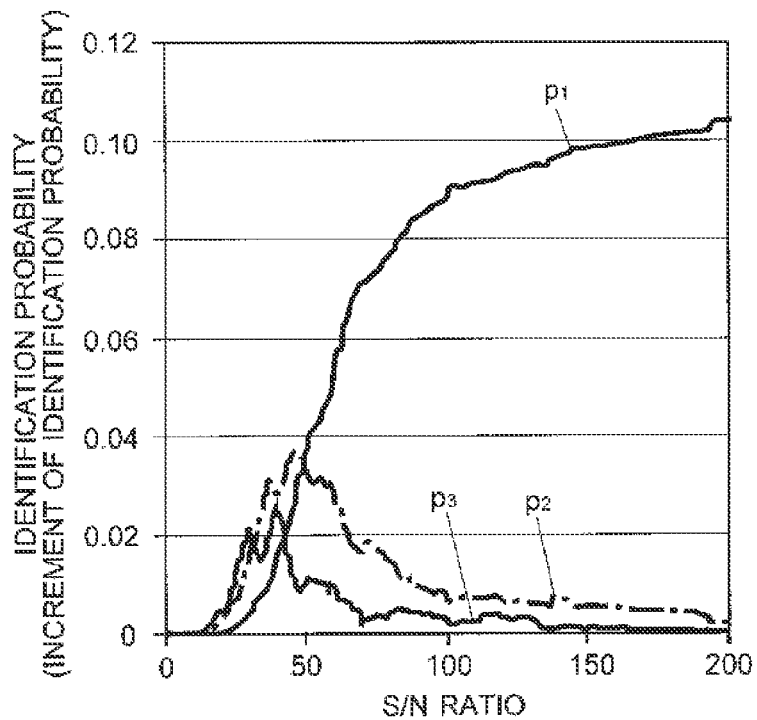
FIG. 9 shows a relationship between the estimated value of the identification probability and the signal-to-noise ratio of the $MS^1$ peaks in the case where the number of data accumulation is normal (one time), as well as the relationship between the estimated increment of the identification probability and the signal-to-noise ratio of the $MS^1$ peaks in the case where the number of times of data accumulation is doubled or tripled.

[Step S24] Estimation of Identification Probability from S/N Ratio Based on Identification Probability Estimation Model As already explained, an identification probability estimation model, or the fitting function shown in FIG. 8, can be determined by the parameter a. Converting the horizontal axis of the fitting function into S/N ratios which respectively correspond to the order numbers yields a curve which gives an estimated value $p_1(r^{(1)})$ of the identification probability for a given S/N ratio, where $r^{(1)}$ is the S/N ratio of an $MS^1$ peak. The conversion of the order number into the S/N ratio can be achieved, for example, by using a table which holds information showing the relationship between the order numbers and the S/N ratios of the $MS^1$ peaks. This information can be previously obtained when the $MS^1$ peaks are sorted by S/N ratio. FIG. 9 shows a curve of the estimated value $p_1(r^{(1)})$ of the identification probability computed from the fitting curve shown in FIG. 8. By using this curve, an estimated value of the identification probability is calculated for each $MS^1$ peak from its S/N ratio. The non-smooth form of the curve of the estimated value $p_1(r^{(1)})$ of the identification probability is due to the irregularity in the S/N ratios of the $MS^1$ peaks used for the creation of the identification probability model.

[Step S25] Estimation of Identification Probability Increment which Occurs when Number of Times of Data Accumulations is Increased The estimated value $p_1(r^{(1)})$ of the identification probability calculated in Step S24 is an identification probability under "normal" conditions; i.e. it is a value obtained in the case of using an $MS^2$ spectrum data which has been acquired by the same number of data accumulations as in the case where $MS^2$ spectrum data for the creation of the identification probability estimation model was acquired. That is to say, it is a data obtained by one $MS^2$ measurement, since no accumulation of $MS^2$ spectrum data was performed when the identification probability estimation model was created. In practice, it is possible to perform an $MS^2$ measurement u times for the same precursor ion and accumulate the thereby obtained data. In this case, the number of data accumulation will be u-fold, causing a $\sqrt{u}$-fold increase in the S/N ratio of the $MS^2$ spectrum. Hence, an improvement in the identification probability can be expected. The identification probability in this situation is probably almost equal to the value obtained in the case where the S/N ratio of the $MS^1$ peak is increased to a $\sqrt{u}$-fold value. When the number of times of accumulation of the $MS^2$ spectrum data for the same $MS^1$ peak is doubled (u=2) or tripled (u=3), the identification probability will be expressed as $p_1(\sqrt{2}r^{(1)})$ or $p_1(\sqrt{3}r^{(1)})$, respectively. Accordingly, the estimated values of the identification probability increment for the second and third accumulations of the $MS^2$ spectrum data are respectively given by the following equations (7) and (8).

$$p_2(r^{(1)})=p_1(\sqrt{2}r^{(1)})-p_1(r^{(1)}) \quad (7)$$

$$p_3(r^{(1)})=p_1(\sqrt{3}r^{(1)})-p_1(\sqrt{2}r^{(1)}) \quad (8)$$

An example of the curves of the estimated values $p_2(r^{(1)})$ and $p_3(r^{(1)})$ of the identification probability increment ix shown in FIG. 9.

[Step S26] Determination of Order of Priority of $MS^2$ Measurement for Each $MS^1$ Peak The order of priority of $MS^1$ peaks to be selected as a precursor ion for the actual $MS^2$ measurement is determined, using the estimated value of the identification probability obtained in Step S24 for each $MS^1$ peak in the normal mode of accumulation of $MS^2$ spectrum data (i.e. no accumulation in the present example) and the estimated value of the identification probability increment obtained in Step S25 for each $MS^1$ peak in the second and third accumulations of $MS^2$ spectrum data.

Figure 10A:
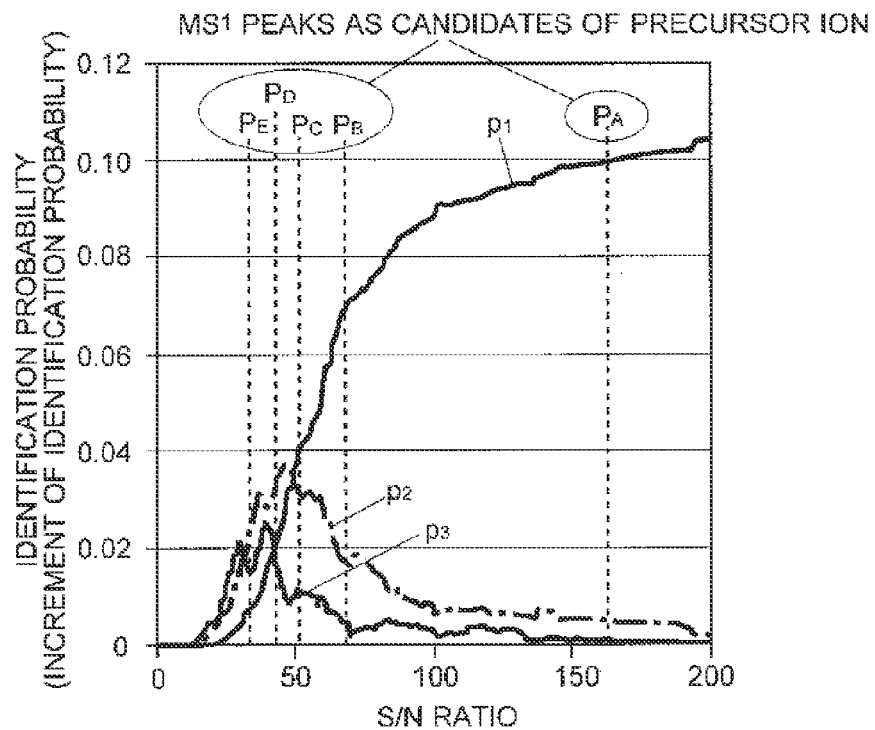
FIGS. 10A and 10B show estimated values of the identification probability for five $MS^{n-1}$ peaks differing in signal-to-noise ratio, as well as estimated increments of the identification probability in the case where the number of times of data accumulation is doubled or tripled.
Figure 10B:
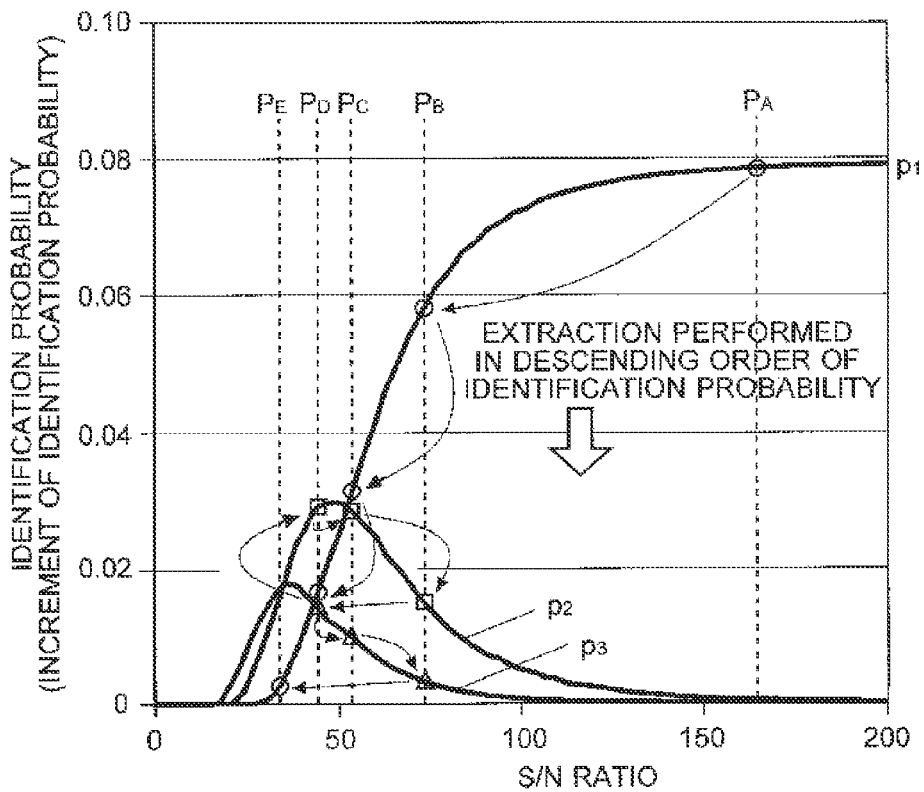

As one example, consider the case where five $MS^1$ peaks $P_A$, $P_B$, $P_C$, $P_D$ and $P_E$ have been selected as the candidates of the precursor ion on an $MS^1$ spectrum obtained for a certain fractionated sample, with the S/N ratios of the five peaks being located as shown in FIGS. 10A and 10B. The graph shown in FIG. 10A is the same as the one shown in FIG. 9, while the graph shown in FIG. 10 B is a graph obtained by smoothing the curves shown in FIG. 10A. The method to be hereinafter described uses FIG. 10B to determine the order of priority of $MS^n$ measurements, although FIG. 10A can also be similarly used.

In FIG. 10B, each intersection at which one of the vertically drawn dashed lines corresponding to the $MS^1$ peaks $P_A$, $P_B$, $P_C$, $P_D$ and $P_E$ intersects with one of the curves $p_1(r^{(1)})$, $p_2(r^{(1)})$ and $p_3(r^{(1)})$ indicates the estimated value of either the identification probability or the identification probability increment for the corresponding $MS^1$ peak. Accordingly, the estimated value of the identification probability or that of the identification probability increment at each point is sequentially extracted in descending order of the probability of successful identification, i.e. in the direction as indicated by the downward arrow in FIG. 10B, and this order is used as the order of priority of the $MS^2$ measurements each of which uses one of the $MS^1$ peaks as the precursor ion. It should be noted that, for a given $MS^1$ peak, the estimated value of the identification probability increment is only applicable to the second and subsequent $MS^2$ measurements. Even if one estimated value of the identification probability increment exceeds one estimated value of the identification probability, the former estimated value cannot be extracted until the latter estimated value is extracted.

In the example of FIG. 10B, four $MS^1$ peaks $P_A$, $P_B$, $P_C$, and $P_D$ are initially extracted on the curve $p_1(r^{(1)})$ in descending order of the probability of successful identification. It should be noted that the extracted points on the curve $p_1(r^{(1)})$ (i.e. the aforementioned intersection) are represented by circles in FIG. 10B. A further movement toward lower levels of the identification probability reveals that the estimated value of the identification probability increment corresponding to the peak $P_D$ on the curve $p_2(r^{(1)})$ is higher than the estimated value of the identification probability corresponding to the peak $P_E$ on the curve $p_1(r^{(1)})$. This means that the identification probability achieved by performing the second $MS^2$ measurement using the $MS^1$ peak $P_D$ as the precursor ion and accumulating the data of $MS^2$ spectra is higher than that achieved by performing the first $MS^2$ measurement using the $MS^1$ peak $P_E$ as the precursor ion. Accordingly, one $MS^1$ peak $P_D$ is extracted on the curve $p_2(r^{(1)})$, and subsequently, two $MS^1$ peaks $P_C$ and $P_B$ are sequentially extracted on the curve $p_2(r^{(1)})$ for the same reason. In FIG. 10B, the extracted points on the curve $p_2(r^{(1)})$ (i.e. the aforementioned intersection) are represented by squares.

A further movement toward lower levels of the identification probability reveals that the estimated value of the identification probability increment corresponding to the peak $P_D$ on the curve $p_3(r^{(1)})$ is higher than the estimated value of the identification probability corresponding to the peak $P_E$ on the curve $p_1(r^{(1)})$. This means that the identification probability achieved by performing the third $MS^2$ measurement using the $MS^1$ peak $P_D$ as the precursor ion and accumulating the data of $MS^2$ spectra is higher than that achieved by performing the first $MS^2$ measurement using the $MS^1$ peak $P_E$ as the precursor ion. Accordingly, one $MS^1$ peak $P_D$ is extracted on the curve $p_3(r^{(1)})$, and subsequently, two $MS^1$ peaks $P_C$ and $P_B$ are sequentially extracted on the curve $p_3(r^{(1)})$ for the same reason. In FIG. 10B, the extracted points on the curve $p_3(r^{(1)})$ (i.e. the aforementioned intersection) are represented by triangles.

A further movement toward lower levels of the identification probability reveals that the estimated value of the identification probability corresponding to the $MS^1$ peak $P_E$ on the curve $p_1(r^{(1)})$ is the highest. At this point, the $MS^1$ peak $P_E$ on the curve $p_1(r^{(1)})$ is finally extracted. Subsequently, the $MS^1$ peak $P_E$ on the curve $p_2(r^{(1)})$, which shows an identification probability higher than the estimated value of the identification probability corresponding to the $MS^1$ peak $P_E$ on the curve $p_1(r^{(1)})$, is extracted, and subsequently, the $MS^1$ peak $P_E$ on the curve $p_3(r^{(1)})$ is extracted for the same reason.

In summary, the order of priority of the $MS^2$ measurement according to the estimated values of the identification probability and those of the identification probability increment is as follows:

(i) The first $MS^2$ measurement is sequentially performed for $P_A$, $P_B$, $P_C$ and $P_D$.

(ii) The second $MS^2$ measurement is sequentially performed for $P_D$, $P_C$ and $P_B$, and the obtained data of $MS^2$ spectra are accumulated.

(iii) The third $MS^2$ measurement is sequentially performed for $P_D$, $P_C$ and $P_B$, and the obtained data of $MS^2$ spectra are accumulated.

(iv) The first $MS^2$ measurement for $P_E$ is performed.

(v) The second $MS^2$ measurement for $P_E$ is performed, and the obtained data of $MS^2$ spectra are accumulated.

(vi) The third $MS^2$ measurement for $P_E$ is performed, and the obtained data of $MS^2$ spectra are accumulated.

Thus, the order of priority of the $MS^2$ measurement to be performed for each of a plurality of $MS^1$ peaks selected as the candidates of the precursor ion can be determined by using the S/N ratio of each $MS^1$ peak and the curves each of which shows the relationship between the S/N ratios and the estimated values of the identification probability or those of the identification probability increment based on the identification probability estimation model.

[Step S27] Optimization of $MS^2$ Measurement Sequence

Although the order of priority of the $MS^2$ measurements can be determined in Step S26, all the $MS^2$ measurements cannot always be actually performed according to that order of priority. This is due to the fact that the number of $MS^1$ peaks extracted as the precursor ions on an $MS^1$ spectrum obtained from one fractionated sample is irregular, whereas the length of measurement time, the data-processing time for identification and/or the number of times of the measurement is normally limited. To deal with this problem, optimization of the $MS^2$ measurement sequence, which defines the order of $MS^2$ measurements for a plurality of precursor ions, is performed by imposing a condition on the number of times of the $MS^2$ measurements for one fractionated sample. An "optimal" measurement sequence is such a measurement sequence that maximizes the estimated value of the total number of substances to be identified (which are peptides in the present example), under the specified limitation on the number of times of the $MS^2$ measurements. The previously described case of five $MS^1$ peaks $P_A$, $P_B$, $P_C$, $P_D$ and $P_E$ being present as the candidates of the precursor ion is hereinafter described by way of illustration.

Now, suppose that an $MS^2$ measurement can be performed up to nine times for one fractionated sample; in other words, the upper limit of the number of times of the $MS^2$ measurements is nine. According to the order of priority determined in Step S26, the $MS^2$ measurements of (i) through (iii) can be performed under this limitation. Accordingly, the optimal sequence of the $MS^2$ measurements is as follows: for $MS^1$ peak $P_A$, the $MS^2$ measurement is performed only one time and no accumulation of $MS^2$ spectrum data is performed; for $MS^1$ peak $P_B$, the $MS^2$ measurement is performed two times and the obtained data of $MS^2$ spectra are accumulated (double accumulation); and for each of the $MS^1$ peaks $P_C$ and $P_D$, the $MS^2$ measurement is performed three times and the obtained data of $MS^2$ spectra are accumulated (triple accumulation). However, it should be noted that, in some type of ion source (e.g. a MALDI source), repeating the $MS^2$ measurement for the same fractionated sample tends to degrade the sample and cause a decrease in the signal intensity. Therefore, it is preferable to preferentially perform the $MS^2$ measurement for $MS^1$ peaks having relatively low S/N ratios. If such a degradation of the sample is taken into account, the measurement sequence for performing an $MS^2$ measurement nine times will include the consecutive steps of performing the $MS^2$ measurement three times for $MS^1$ peak $P_D$, three times for $MS^1$ peak $P_C$, two times for $MS^1$ peak $P_B$, and only one time for $MS^1$ peak $P_A$.

As another example, consider the case where an $MS^2$ measurement can be performed up to twelve times for one fractionated sample; in other words, the upper limit of the number of times of the $MS^2$ measurements is twelve. According to the aforementioned order of priority, the $MS^2$ measurements of (i) through (v) can be performed under this limitation. Accordingly, the optimal sequence of the $MS^2$ measurements is as follows: for $MS^1$ peak $P_A$, the $MS^2$ measurement is performed only one time and no accumulation of $MS^2$ spectrum data is performed; for $MS^1$ peak $P_E$, the $MS^2$ measurement is performed two times and the obtained data of $MS^2$ spectra are accumulated (double accumulation); and for each of the $MS^1$ peaks $P_B$, $P_C$ and $P_D$, the $MS^2$ measurement is performed three times and the obtained data of $MS^2$ spectra are accumulated (triple accumulation). If the degradation of the sample is taken into account, the measurement sequence for performing an $MS^2$ measurement twelve times will include the consecutive steps of performing the $MS^2$ measurement two times for $MS^1$ peak $P_E$, three times for MS¹ peak $P_D$, three times for MS¹ peak $P_C$, three times for MS¹ peak $P_B$, and only one time for MS¹ peak $P_A$.

From the descriptions so far, qualitative criteria for optimizing the MS² measurement sequence can be summarized as follows:

(1) For an MS¹ peak having a high S/N ratio, the MS² measurement should be performed only one time. For an MS¹ peak whose S/N ratio lies near the peak of the curve $p_2(r^{(1)})$ in FIGS. 10A and 10B, the MS² measurement should be performed two times and the obtained data should be double-accumulated. For an MS¹ peak whose S/N ratio lies near the peak of the curve $p_3(r^{(1)})$, the MS² measurement should be performed three times and the obtained data should be triple-accumulated.

(2) If the total number of MS² measurements allowed to be performed is small, an MS¹ peak which requires no accumulation of the data of MS² spectra (i.e. whose S/N ratio is high) should be preferentially selected as the target of the MS² measurement. If the total number of MS² measurements allowed to be performed is large, an MS¹ peak for which the optimal number of times of the MS² measurement is two or three (i.e. whose S/N ratio is relatively low) may also be selected.

The optimal MS² measurement sequence is determined before the MS² measurement for the fractionated sample concerned is initiated, i.e. without actually performing the MS² measurement. Determining the sequence merely requires referring to a previously known identification probability estimation model. Although the estimation is highly reliable, it does not always ensure that an optimal MS² measurement sequence determined for a certain fractionated sample is absolutely correct. Therefore, at a certain stage in the sequence of MS² measurements performed for a certain fractionated sample, the order of the subsequent MS² measurements may be once more optimized, based on the results of identification that have already been obtained for that fractionated sample.

Thus, by the substance identification method according to the present invention, an appropriate order and number of times of MS² measurements using a plurality of MS¹ peaks as precursor ions can be determined before the actual execution of the MS² measurements so as to maximize or nearly maximize the number of substances to be identified, by determining parameters of an identification probability estimation model in advance of the measurement of a target sample and performing simple computations and processes using that identification probability estimation model. The substance identification can be very efficiently performed by conducting MS² measurements using the precursor ions selected according to the determined MS² measurement sequence, and performing the substance identification process using the measured results.

Figure 1:
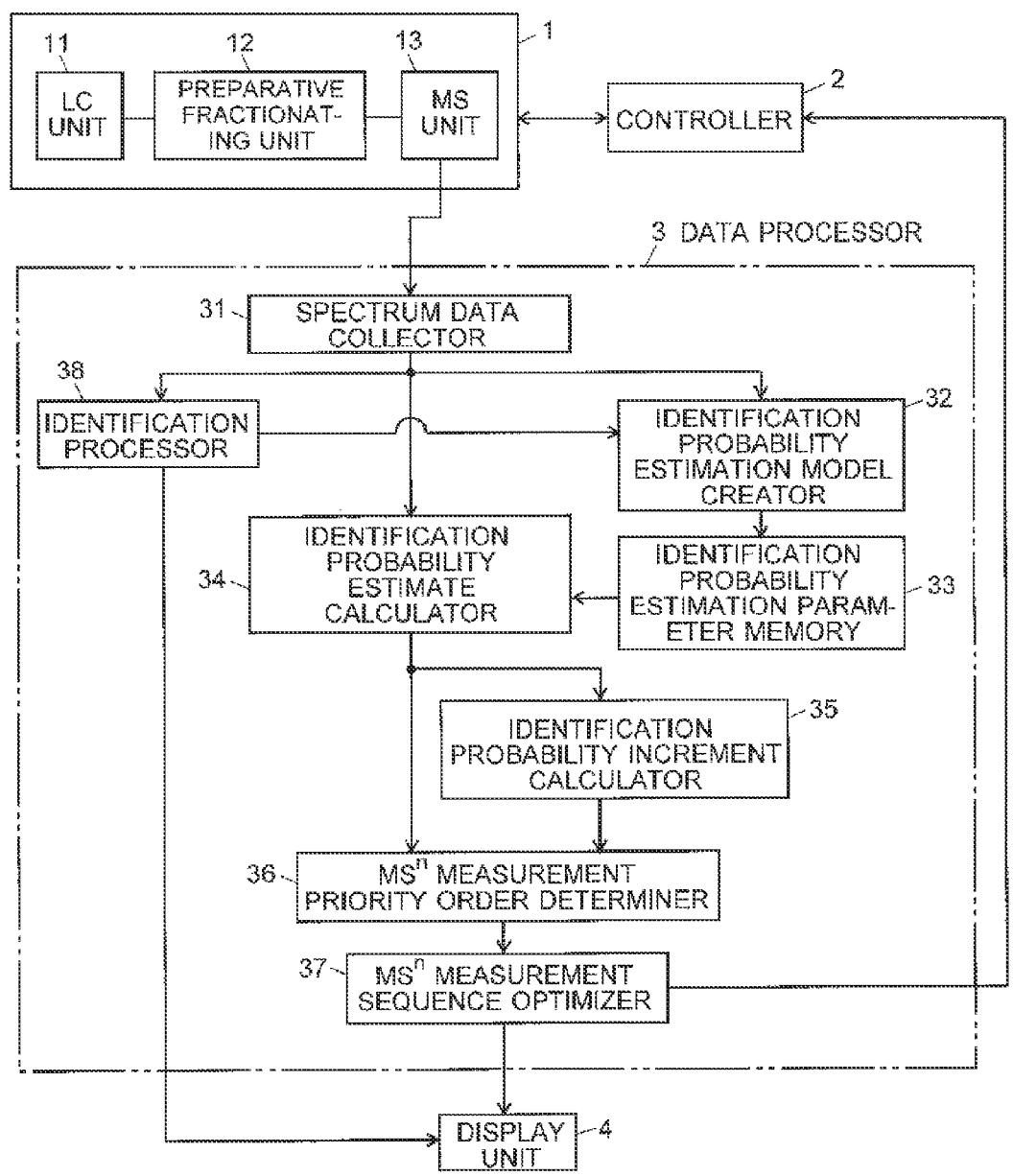
FIG. 1 is a block diagram schematically showing the configuration of a mass spectrometry system for carrying out the substance identification method according to the present invention.

One embodiment of the mass spectrometry system for carrying out the previously described substance identification method is hereinafter described by means of FIG. 1. FIG. 1 is a schematic configuration diagram of the mass spectrometry system according to the present embodiment.

In FIG. 1, an analyzer section 1 includes a liquid chromatograph (LC) unit 11 for separating various kinds of substances in a liquid sample according to their retention time, a preparative fractionating unit 12 for preparative-fractionating the sample containing the substances separated by the LC unit 11 to prepare a plurality of different fractionated samples, and a mass spectrometer (MS) unit 13 for selecting one of the fractionated samples and performing a mass spectrometry for the selected sample. Though not shown, the MS unit 13 is a MALDI-IT-TOFMS including a MALDI ion source, an ion trap (IT) and a time-of-flight mass spectrometer (TOFMS). This unit is capable of not only an MS¹ measurement but also an MSⁿ measurement in which the selection of a precursor ion and the operation of collision induced dissociation (CID) are performed one or more times and then the mass spectrometry is performed by the TOFMS. In the case where MS¹ and MS² measurements only need to be performed (i.e. when there is no need to perform an MSⁿ measurement with n=3 or greater), a mass spectrometer with a simpler configuration may be used, such as a triple quadrupole mass spectrometer, in place of the combination of the ion trap and the TOFMS.

A controller 2 controls the operations of each unit of the analyzer section 1. Data obtained with the MS unit 13 of the analyzer section 1 are sent to and processed by a data processor 3. The result of this data processing is outputted, for example, on a display unit 4. The data processor 3 includes the following functional blocks: a spectrum data collector 31 for collecting measurement data, such as MS¹ or MSⁿ spectrum data; an identification probability estimation model creator 32 for performing the processes of Steps S12 through S16; an identification probability estimation parameter memory 33 for holding parameters obtained with the identification probability estimation model creator 32; an identification probability estimate calculator 34 for performing processes corresponding to Steps S22 through S24; an identification probability increment calculator 35 for performing a process corresponding to Step S25; an MSⁿ measurement priority order determiner 36 for performing a process corresponding to Step S26; an MSⁿ measurement sequence optimizer 37 for performing a process corresponding to Step S27; and an identification processor 38 for performing an identifying process according to a predetermined algorithm. The data processor 3 and the controller 2 may be realized by using a personal computer as hardware resources on which the aforementioned functional blocks are embodied by running a previously installed dedicated controlling and processing software program.

Prior to the comprehensive identification for a target sample, the analyzer section 1 under the control of the controller 2 performs MS¹ and MS² measurements for each fractionated sample obtained from a preparatory sample for the creation of an identification probability estimation model. The identification processor 38 performs an identifying process based on the collected data of MS¹ and MS² spectra. The identification probability estimation model creator 32 creates an identification probability estimation model based on the spectrum data and the result of identification. Then, one or more parameters for reproducing this identification probability estimation model are stored in the identification probability estimation parameter memory 33.

In the comprehensive identification of the target sample, the analyzer section 1 under the control of the controller 2 initially performs an MS¹ measurement for each fractionated sample obtained from the target sample, and the spectrum data collector 31 collects MS¹ spectrum data. For each set of MS¹ spectrum data obtained from one fractionated sample, the identification probability estimate calculator 34 calculates an estimated value of the identification probability for each of a plurality of MS¹ peaks selected as the candidates of the precursor ion, using the identification probability estimation model reproduced from the parameters read from the identification probability estimation parameter memory 33. This model is also used by the identification probability increment calculator 35 in calculating an estimated value of the identification probability increment which is expected to be obtained if the MS² measurement is performed two or three times for the same $MS^1$ peak and the obtained data are accumulated. The $MS''$ measurement priority order determiner 36 determines, for each fractionated sample, an order of priority of $MS^2$ measurements from the estimated values of the identification probability as well as those of the identification probability increment for the plurality of $MS^1$ peaks. The $MS''$ measurement sequence optimizer 37 determines, for each fractionated sample, an optimal $MS^2$ measurement sequence which maximizes the number of substances to be identified, taking into account additional conditions, such as the limitation on the number of times of the $MS''$ measurements and/or the necessity of considering sample degradation.

The optimal $MS^2$ measurement sequence which has been determined for each fractionated sample in the previously described manner is sent to the controller 2. According to this $MS^2$ measurement sequence, the controller 2 controls the analyzer section 1 to conduct $MS^2$ measurements for each fractionated sample obtained from the target sample. The identification processor 38 performs the process of identifying the substances in the target sample, based on the previously collected $MS^1$ spectrum data obtained for each fractionated sample originating from the target sample as well as the newly collected $MS^2$ spectrum data obtained for each fractionated samples originating from the target sample. The result of this identification is shown on the screen of the display unit 4. Thus, as compared to conventional systems, the mass spectrometry system according to the present embodiment can identify a larger number of substances within a limited length of time or with a limited number of times of the measurement.

In the operation of the previously described embodiment, an $MS^2$ measurement according to an optimal $MS^2$ measurement sequence is automatically initiated after this sequence is determined. Alternatively, it is possible to temporarily show the optimal $MS''$ measurement sequence on the screen of the display unit 4 and defer the initiation of the $MS^2$ measurements and identifications for the target sample until a user (analysis operator) enters a command for initiating the $MS^2$ measurement. Such a system allows users to appropriately modify the $MS^2$ measurement sequence according to their own judgments or experiences before executing the $MS^2$ measurements.

For ease of explanation, the previous embodiment took the simplest example of estimating the identification probabilities of $MS^1$ peaks and determining an optimal $MS^2$ measurement sequence from the estimated result. It is evident that the previously described method can be extended to the case where an identification probability is estimated for each of the $MS^{n-1}$ peaks selected as the precursor ions for $MS''$ measurements and an optimal $MS''$ measurement sequence is determined from the estimated result before the $MS''$ measurements are actually performed.

It should be noted that the previously described embodiment is a mere example of the present invention, and any change, modification or addition appropriately made within the spirit of the present invention will naturally fall within the scope of claims of the present patent application.

EXPLANATION OF NUMERALS

1 . . . Analyzing Section
11 . . . Liquid Chromatograph (LC) Unit
12 . . . Preparative Fractionating Unit
13 . . . Mass Spectrometer (MS) Unit
2 . . . Controller
3 . . . Data Processor
31 . . . Spectrum Data Collector
32 . . . Identification Probability Estimation Model Creator
33 . . . Identification Probability Estimation Parameter Memory
34 . . . Identification Probability Estimate Calculator
35 . . . Identification Probability Increment Calculator
36 . . . $MS''$ Measurement Priority Order Determiner
37 . . . $MS''$ Measurement Sequence Optimizer
38 . . . Identification Processor
4 . . . Display Unit

The invention claimed is:

1. A substance identification method for identifying a substance contained in each of a plurality of fractionated samples obtained by separating various substances contained in a sample according to a predetermined separation parameter comprising:

a) an identification probability estimation model creation step, in which an identification probability estimation model is created by using peak information values showing information on $MS^{n-1}$ peaks found by $MS^{n-1}$ measurements (where n is an integer equal to or greater than two) for a plurality of fractionated samples obtained from a predetermined sample and results of substance identification based on results of $MS''$ measurements using each of the $MS^{n-1}$ peaks as a precursor ion, the model showing a relationship between peak information values of a plurality of $MS^{n-1}$ peaks originating from a same kind of sample and a cumulative number of peaks successfully identified through a series of $MS''$ measurements and identifications in which the $MS^{n-1}$ peaks are sequentially selected as a precursor ion in order of the s peak information values thereof, and identification probability estimation model information representing the identification probability estimation model is stored;

b) a peak information value acquisition step, in which, after an $MS^{n-1}$ measurement for at least one fractionated sample obtained from a target sample to be identified has been completed, peak information value is obtained for each of a plurality of $MS^{n-1}$ peaks selected as candidates of the precursor ion from among the $MS^{n-1}$ peaks found by the $MS^{n-1}$ measurement;

c) an identification probability estimation step, in which an estimated value of the identification probability of each of the $MS^{n-1}$ peaks is calculated from the peak information values of the $MS^{n-1}$ peaks obtained in the peak information value acquisition step, with reference to the identification probability estimation model derived from the identification probability estimation model information;

d) an identification probability increment estimation step, in which an estimated increment of the identification probability, which shows a degree of increase in the identification probability achieved by performing an $MS''$ measurement for a same $MS^{n-1}$ peak a plurality of times and accumulating the results of the measurement, is calculated from the estimated value of the identification probability calculated for each of a plurality of $MS^{n-1}$ peaks selected as the candidates of the precursor ion in the identification probability estimation step;

e) an $MS''$ measurement order determination step, in which, for each of a plurality of $MS^{n-1}$ peaks selected as the candidates of the precursor ion, an order of priority of the $MS''$ measurements for a plurality of $MS^{n-1}$ peaks under the condition that a plurality of $MS''$ measurements are allowed for the same $MS^{n-1}$ peak is determined based on the estimated value of the identification probability of each MS$^{n-1}$ peak calculated in the identification probability estimation step and the increment of the identification probability estimated in the identification probability increment estimation step;

f) an MS$^n$ spectrum acquisition step, in which MS$^n$ spectra are obtained by performing an MS$^n$ measurement for each of a plurality of fractionated samples obtained by separating the target sample to be identified according to the predetermined separation parameter and fractionating the sample, using the order of priority determined in the MS$^n$ measurement order determination step; and g) a substance identification step, in which a substance contained in each of the plurality of fractionated samples is identified based on the MS$^n$ spectra obtained in the MS$^n$ spectrum acquisition step.

2. The substance identification method according to claim 1, further comprising:

an MS$^n$ measurement sequence determination step, in which a measurement sequence for performing MS$^n$ measurements for a plurality of MS$^{n-1}$ peaks is determined, based on the order of priority determined in the MS$^n$ measurement order determination step and the peak information value of each MS$^{n-1}$ peak, under an upper limit of the number of times of the MS$^n$ measurements to be performed for one fractionated sample.

3. The substance identification method according to claim 1, wherein:

a measurement for a predetermined sample is performed before the measurement for the target sample, and based on a result of the former measurement, the identification probability estimation model is created in the identification probability estimation model creation step.

4. The substance identification method according to claim 1, wherein:

a measurement sequence of the MS$^n$ measurement for a fractionated sample is determined by a sequential process of the peak information value acquisition step, the identification probability estimation step, the MS$^n$ measurement order determination step and the MS$^n$ measurement sequence determination step before the MS$^n$ measurement for that fractionated sample is actually performed.

5. The substance identification method according to claim 4, wherein:

a measurement sequence of the MS$^n$ measurement for a fractionated sample is determined by a sequential process of the peak information value acquisition step, the identification probability estimation step, the MS$^n$ measurement order determination step and the MS$^n$ measurement sequence determination step before the MS$^n$ measurement for that fractionated sample is performed; and after the MS$^n$ measurement according to the measurement sequence is initiated, the measurement sequence is modified by using an identification result obtained in a course of the MS$^n$ measurement.

6. The substance identification method according to claim 1, wherein:

the peak information values showing the information on MS$^{n-1}$ peaks are signal-to-noise ratios.

7. A mass spectrometry system used for identifying a substance or substances contained in each of a plurality of fractionated samples obtained by separating various substances contained in a sample according to a predetermined separation parameter, comprising:

a) an identification probability estimation model information memory for storing identification probability estimation model information representing an identification probability estimation model which shows a relationship between peak information values of a plurality of MS$^{n-1}$ peaks originating from a same kind of sample and a cumulative number of MS$^n$ peaks successfully identified through a series of MS$^n$ measurements and identifications in which the MS$^{n-1}$ peaks are sequentially selected as a precursor ion in order of the peak information values thereof, the identification probability estimation model being created by using the peak information values showing information on MS$^{n-1}$ peaks found by MS$^{n-1}$ measurements (where n is an integer equal to or greater than two) for a plurality of fractionated samples obtained from a predetermined sample and results of substance identification based on results of MS$^n$ measurements using each of the MS$^{n-1}$ peaks as a precursor ion;

b) a peak information value obtainer, which, after an MS$^{n-1}$ measurement for at least one fractionated sample obtained from a target sample to be identified has been completed, obtains a peak information value for each of a plurality of MS$^{n-1}$ peaks selected as candidates of the precursor ion from among the MS$^{n-1}$ peaks found by the MS$^{n-1}$ measurement;

c) an identification probability estimator for calculating an estimated value of the identification probability of each of the MS$^{n-1}$ peaks from the peak information values of the MS$^{n-1}$ peaks obtained by the peak information value obtainer, with reference to the identification probability estimation model derived from the identification probability estimation model information;

d) an identification probability increment estimator, in which an estimated increment of the identification probability, which shows a degree of increase in the identification probability achieved by performing an MS$^n$ measurement for a same MS$^{n-1}$ peak a plurality of times and accumulating the results of the measurement, is calculated from the estimated value of the identification probability calculated for each of a plurality of MS$^{n-1}$ peaks selected as the candidates of the precursor ion by the identification probability estimator;

e) an MS$^n$ measurement order determiner for determining an order of priority of the MS$^n$ measurements of the plurality of MS$^{n-1}$ peaks as the candidates of the precursor ion, under the condition that a plurality of MS$^n$ measurements are allowed for the same MS$^{n-1}$ peak, based on the estimated value of the identification probability of each MS$^{n-1}$ peak calculated by the identification probability estimator and the increment of the identification probability estimated by the identification probability increment estimator;

f) an MS$^n$ spectrum obtainer for obtaining MS$^n$ spectra by performing an MS$^n$ measurement for each of a plurality of fractionated samples obtained by separating the target sample to be identified according to the predetermined separation parameter and fractionating the sample, using the order of priority determined in the MS$^n$ measurement order determiner; and g) a substance identifier for identifying a substance contained in each of the plurality of fractionated samples based on the MS$^n$ spectra obtained in the MS$^n$ spectrum obtainer.

8. The mass spectrometry system according to claim 7, further comprising:

an $MS^n$ measurement sequence determiner, in which a measurement sequence for performing $MS^n$ measurements for a plurality of $MS^{n-1}$ peaks is determined, based on the order of priority determined by the $MS^n$ measurement order determiner and the peak information value of each $MS^{n-1}$ peak, under an upper limit of the number of times of the $MS^n$ measurements to be performed for one fractionated sample.

9. The mass spectrometry system according to claim 7, wherein:

a measurement for a predetermined sample is performed before the measurement for the target sample, and based on a result of the former measurement, the identification probability estimation model is created by the identification probability estimation model creator.

10. The mass spectrometry system according to claim 7, wherein:

a measurement sequence of the $MS^n$ measurement for a fractionated sample is determined by a sequential process performed by the peak information value obtainer, the identification probability estimator, the $MS^n$ measurement order determiner and the $MS^n$ measurement sequence determiner before the $MS^n$ measurement for that fractionated sample is actually performed.

11. The mass spectrometry system according to claim 10, wherein:

a measurement sequence of the $MS^n$ measurement for a fractionated sample is determined by a sequential process performed by the peak information value obtainer, the identification probability estimator, the $MS^n$ measurement order determiner and the $MS^n$ measurement sequence determiner before the $MS^n$ measurement for that fractionated sample is performed; and after the $MS^n$ measurement according to the measurement sequence is initiated, the measurement sequence is modified by using an identification result obtained in a course of the $MS^n$ measurement.

12. The mass spectrometry system to claim 7, wherein:

the peak information values showing the information on $MS^{n-1}$ peaks are signal-to-noise ratios.

* * * * *